United States Patent
Kunkel et al.

(10) Patent No.: US 8,697,387 B2
(45) Date of Patent: Apr. 15, 2014

(54) METHODS FOR IDENTIFYING AGENTS AND THEIR USE FOR THE PREVENTION OF RESTENOSIS

(75) Inventors: Eric J. Kunkel, San Mateo, CA (US); Evangelos Hytopoulos, San Mateo, CA (US); Ivan Plavec, Sunnyvale, CA (US)

(73) Assignee: DiscoverRx Corporation, Fremont, CA (US)

( * ) Notice: Subject to any disclaimer, the term of this patent is extended or adjusted under 35 U.S.C. 154(b) by 1019 days.

(21) Appl. No.: 12/302,756

(22) PCT Filed: Jun. 4, 2007

(86) PCT No.: PCT/US2007/013230
§ 371 (c)(1),
(2), (4) Date: Aug. 3, 2009

(87) PCT Pub. No.: WO2007/143211
PCT Pub. Date: Dec. 13, 2007

(65) Prior Publication Data
US 2009/0304769 A1 Dec. 10, 2009

Related U.S. Application Data

(60) Provisional application No. 60/810,508, filed on Jun. 2, 2006, provisional application No. 60/938,031, filed on May 15, 2007.

(51) Int. Cl.
*C12Q 1/02* (2006.01)
*C12N 5/00* (2006.01)

(52) U.S. Cl.
USPC .............................................. 435/29; 435/375

(58) Field of Classification Search
USPC ..................................................... 435/375, 29
See application file for complete search history.

(56) References Cited

U.S. PATENT DOCUMENTS

| | | | |
|---|---|---|---|
| 5,498,238 A | 3/1996 | Shapland et al. | |
| 5,891,108 A | 4/1999 | Leone et al. | |
| 5,972,027 A | 10/1999 | Johnson | |
| 5,985,833 A | 11/1999 | Mosesson et al. | |
| 6,004,346 A | 12/1999 | Wolff et al. | |
| 6,060,451 A | 5/2000 | DiMaio et al. | |
| 6,071,305 A | 6/2000 | Brown et al. | |
| 6,147,109 A | 11/2000 | Liao et al. | |
| 6,174,855 B1 | 1/2001 | Hansson | |
| 6,201,006 B1 | 3/2001 | Koo et al. | |
| 6,232,315 B1 | 5/2001 | Shafer et al. | |
| 6,258,121 B1 | 7/2001 | Yang et al. | |
| 6,273,913 B1 | 8/2001 | Wright et al. | |
| 6,280,411 B1 | 8/2001 | Lennox | |
| 6,326,386 B1 | 12/2001 | Watson et al. | |
| 6,335,029 B1 | 1/2002 | Kamath et al. | |
| 6,656,695 B2 | 12/2003 | Berg et al. | |
| 6,763,307 B2 | 7/2004 | Berg et al. | |
| 6,801,859 B1 * | 10/2004 | Friend et al. | 702/19 |
| 2002/0119178 A1 * | 8/2002 | Levesque et al. | 424/423 |
| 2004/0063088 A1 | 4/2004 | Berg et al. | |

FOREIGN PATENT DOCUMENTS

| | | |
|---|---|---|
| WO | 01/67103 A1 | 9/2001 |
| WO | 03/023573 A2 | 3/2003 |
| WO | 2004/022711 A2 | 3/2004 |
| WO | 2004/094609 A2 | 11/2004 |
| WO | 2004/094992 A2 | 11/2004 |
| WO | 2005/023987 A2 | 3/2005 |
| WO | 2005/093561 A1 | 10/2005 |

OTHER PUBLICATIONS

Kusch et al., Impact and signal transduction pathways of the uPA/uPAR system in arteriosclerosis and restenosis. Zeitschrift fur Kardiologie, vol. 90 No. 5 (2001) p. 307-318.*
Stoll et al., Endotoxin, TLR4 signaling and vascular inflammation: potential therapeutic targets in cardiovascular disease. Current Pharmaceutical Design, vol. 12 No. 32 (2006) pp. 4229-4245.*
LaFont et al., Endothelial dysfunction and collagen accumulation: Two independent factors for restenosis and constrictive remodeling after experimental angioplasty. Circulation, vol. 100 (1999) pp. 1109-1115.*
Pan, Shiow-Lin, et al., "Esculetin Inhibits Ras-Mediated Cell Proliferation and Attenuates Vascular Restenosis Following Angioplasty in Rats," Biochemical Pharmacology, vol. 65, No. 11, Jun. 1, 2003, pp. 1897-1905.
Jaschke, Birgit, et al., "Local statin therapy differentially interferes with smooth muscle and endothelial cell proliferation and reduces neointima on a drug-eluting stent platform," Cardiovascular Research, Oxford University Press, vol. 68, No. 3, Dec. 1, 2005, pp. 483-492.
Mintzer, R.J., et al., "Differential Effects of IFN-β1b on the Proliferation of Human Vascular Smooth Muscle and Endothelial Cells," Journal of Interferon and Cytokine Research, vol. 18, No. 11, Nov. 1998, pp. 939-945.
Supplementary European Search Report, Appl. No. EP 07 80 9331, May 19, 2009, 2 pp.

* cited by examiner

*Primary Examiner* — Jon P Weber
*Assistant Examiner* — Kara Johnson
(74) *Attorney, Agent, or Firm* — David J. Aston; Peters Verny, LLP

(57) ABSTRACT

Agents that inhibit or prevent restenosis are identified by assaying test agents in a battery of assays to measure the effect of the test agent on cell proliferation, thrombosis, tissue modeling, and inflammation. Treatment for restenosis is provided using compositions of the invention.

5 Claims, No Drawings

METHODS FOR IDENTIFYING AGENTS AND THEIR USE FOR THE PREVENTION OF RESTENOSIS

BACKGROUND OF THE INVENTION

1. Field of the Invention

The present invention provides methods for identifying agents that prevent restenosis, and the use of one or more agents identified in the screen, including without limitation colchicine analogs as defined herein, in the treatment or prevention of restenosis and so relates to the fields of biology, molecular biology, chemistry, medicinal chemistry, pharmacology, and medicine.

2. Description of Related Disclosures

The success of stents in balloon angioplasty has been limited by thrombotic complications and restenosis of the vessel wall, both of which occur as a result of normal injury and repair processes. Anti-platelet drugs and procedural anticoagulation have reduced the incidence of in-stent thrombosis, while drug-eluting stents have significantly reduced the incidence of restenosis. Currently approved drugs used on drug-eluting stents (paclitaxel, rapamycin) are strongly antiproliferative, effectively inhibit smooth muscle proliferation and block neointimal hyperplasia. Antiproliferative drugs, however, may delay or prevent complete healing of the injured vessel. Accordingly, the perpetuation of the wounded vessel can result in late loss (progressive loss of vessel diameter due to neointimal thickening) and late thrombosis, increasing the frequency of follow-up target lesion revascularization procedures, and thus reducing the effectiveness of stents coated with such drugs.

The biological processes that contribute to restenosis and late stage thrombosis include platelet and inflammatory cell recruitment and activation, cell proliferation and migration, vascular remodeling, and compromised re-endothelialization with reduced endothelial cell function. Inhibition of proliferation (e.g. smooth muscle cells, inflammatory cells) is a key process, as the drugs that have been successfully employed in drug-eluting stents (e.g. rapamycin, paclitaxel, everolimus) are strong anti-proliferatives.

Drugs that have been tested on drug eluting stents include agents from several categories: anti-proliferative (paclitaxel, actinomycin D, 17β-estradiol, imatinib mesylate), anti-proliferative/immunosuppressive (rapamycin, FK-506, mycophenolic acid), anti-inflammatory (methylprednisolone, dexamethasone, tranilast), anti-thrombotic (hirudin, iloprost), and others (rosiglitazone) (Abizaid, 2004, D'Amato, 1994, Serruys, 2004, Sousa, 2003a, 2003b). While paclitaxel, rapamycin and everolimus have been shown to be effective and approved for clinical use, other compounds, including some from the same classes have failed (e.g. actinomycin D, mycophenolic acid). Blocking inflammatory processes alone (e.g. with glucocorticoids) has not been effective, although inflammatory mediators and growth factors produced by recruited leukocytes and activated cell types do regulate vascular cell functions and can affect the recovery and repair process.

One of the major health risks of approved drug eluting stents, which are coated with taxol or rapamycin, is late thrombosis, which can lead to serious complications including death months to years following stenting procedure. Current treatment to prevent stent-related thrombosis is the use of oral anti-thrombotic agents such as Plavix, which cannot be maintained long term due to side effects or due to other medical procedures such as surgery where anti-thrombotic agents are contraindicated. Since endothelial cells play a key role in controlling thrombosis and fibrinolysis, and provide a non-procoagulant surface, it is believed that the main cause for the late thrombosis is incomplete re-endothelialization on the stented site. Unfortunately, owing to the complex biological processes that affect the function of stents in vivo, there have been no methods developed to date for the efficient identification and use of agents that would be most effective in inhibiting restenosis without compromising complete healing of the wounded vessel.

Human primary cell-based assay systems (BioMAP® Systems) that model in vitro the complex biology of human disease, including biology relevant to inflammation and restenosis, and which can be used for screening and development of drugs eliciting complex biological activities, have been developed: see U.S. Pat. Nos. 6,656,695 and 6,763,307 and PCT publication Nos. 01/67103, 03/23753, 04/22711, 04/63088, 04/94609, 05/23987, 04/94992, 05/93561, each of which is incorporated herein by reference. BioMAP Systems are capable of detecting and distinguishing activities of a broad range of mechanistically diverse compound classes, including anti-proliferative drugs, immunosuppressive drugs, anti-inflammatory drugs etc. For example, see Kunkel et al. (2004) Assay Drug Dev Technol. 2:431-41; and Kunkel et al. (2004). FASEB J. 18:1279-81.

Activity profiling of compounds, including experimental compounds as well as drugs approved for human or veterinary use, in BioMAP Systems, provides an enhanced understanding of the mechanism of action of compounds and allows the identification of compounds which are suitable for a particular therapeutic use, based on the favorable combinations of biological activities which these compounds induce in BioMAP Systems.

There remains a need for stents and other devices intended for in vivo use with better agents and combination of agents to prevent and treat restenosis. The present invention meets these needs.

SUMMARY OF THE INVENTION

The present invention provides a method for identifying an agent useful in preventing restenosis. In the method, the agent is tested in a panel of assays employing multiple different cell types to identify whether a candidate agent possesses the combination of features desired of an anti-restenosis agent, which features include (1) inhibition of smooth muscle proliferation, (2) little or no effect on endothelial cell proliferation, (3) inhibition of matrix remodeling with promotion of wound healing, (3) not pro-thrombotic, and (4) selected anti-inflammatory activities.

Because few agents have all of the desired features of an anti-restenosis agent, the present invention also provides a method for identifying pairs of agents and combinations of two or more agents that collectively provide the desired features of an anti-restenosis agent more effectively than any of the agents acting alone. In this method of the invention, combinations of agents are tested together in the assays, and a subset of the combinations tested is identified that collectively provide the desired set of features.

The present invention also provides stents and other devices intended for in vivo vascular use, e.g. vascular implantation, for use in percutaneous coronary intervention (PCI), etc. which devices are modified to contain one or more agents identified herein or by the methods of the invention as having desired anti-restenotic features. In one embodiment, the present invention provides a stent or other device intended for in vivo use, wherein said stent or device comprises one or more drugs selected from the group consisting of 8-Azaguanine, Amodiaquin Dihydrochloride Dihydrate, Atovaquone, Betulin, Chlorambucil, Ciclopirox Ethanolamine, Cis-(Z)-Flupentixol Dihydrochloride, Clofilium Tosylate, Deferoxamine Mesylate, Doxazosin Mesylate, Esculetin, Monobenzone, Nifedipine, Primaquine Diphosphate, Securinine, Syrosingopine, Terconazole, and a colchicine analog as defined herein, where the preferred set of agents or drugs is selected from a group consisting of, Cis-(Z)-Flupentixol Dihydrochloride, Clofilium Tosylate, Monobenzone, Nifedipine, Primaquine Diphosphate, Securinine, and a colchicine analog as defined herein. A stent or device according to the invention may comprise said one or more drugs as a coating or any other carrier formulation suitable for elution of the drug when positioned in vivo.

In certain embodiments of the invention, a stent or other device for vascular use, e.g. vascular implantation, for use in percutaneous coronary intervention (PCI), etc. is provided, wherein the stent or other device comprises a colchicine analog as defined herein, where such analogs include, without limitation, trimethylcolchicinic acid and its derivatives as further described below.

In another embodiment, the present invention provides a stent or other device intended for in vivo use, vascular use, e.g. vascular implantation, for use in percutaneous coronary intervention (PCI), etc. which device comprises one or more drugs selected from the group: 8-Azaguanine, Amodiaquini Dihydrochloride Dihydrate, Atovaquone, Betulin, Chlorambucil, Ciclopirox Ethanolamine, Cis-(Z)-Flupentixol Dihydrochloride, Clofilium Tosylate, Deferoxamine Mesylate, Doxazosin Mesylate, Esculetin, Monobenzone, Nifedipine, Primaquine Diphosphate, Securinine, Syrosingopine, Terconazole, and a colchicine analog as defined herein in combination with a second biologically active agent. Such agent may include, without limitation, an anti-inflammatory such as a glucocorticoid receptor agonist (e.g. prednisolone, methylprednisolone, budesonide), an anti-proliferative or proliferation modifier (e.g. estradiol), a lipid metabolism modulating drug (e.g. statins), an insulin sensitizer (e.g. rosiglitazone), an anti-thrombotic drug, etc.

The present invention also provides methods and compositions for the treatment or prevention of restenosis utilizing stents and other devices intended for in vivo vascular use, e.g. vascular implantation, for use in percutaneous coronary intervention (PCI), etc. for vascular administration of anti-restenotic agents, where the device is modified to contain a colchicine analog, which analogs include, without limitation, trimethylcolchicinic acid and analogs and derivatives thereof. A stent or device according to the invention may comprise said one or more drugs as a coating or any other carrier formulation suitable for elution of the drug when positioned in vivo. The methods of the invention include the vascular administration to a subject of a pharmaceutical composition comprising a therapeutically effective amount of a colchicine analog is effective to treat, delay or prevent restenosis proximal to the site of administration.

DEFINITIONS

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques as known in the art, e.g. by chromatography. When the compounds described herein contain olefinic double bonds or other centers of geometric asymmetry, and unless specified otherwise, it is intended that the compounds include both E and Z geometric isomers. Likewise, all tautomeric forms are also intended to be included.

As used throughout, "modulation" is meant to refer to an increase or a decrease in the indicated phenomenon (e.g., modulation of a biological activity refers to an increase in a biological activity or a decrease in a biological activity).

As used herein, the terms "treatment," "treating," and the like, refer to obtaining a desired pharmacologic and/or physiologic effect. The effect may be prophylactic in terms of completely or partially preventing a disease or condition, or symptom thereof, and/or may be therapeutic in terms of a partial or complete cure for a condition and/or adverse affect attributable to the condition. "Treatment," as used herein, covers any treatment of a disease or condition in a mammal, particularly in a human, and includes: (a) preventing the condition from occurring in a subject which may be predisposed to the condition but has not yet been diagnosed as having it; (b) inhibiting the development of the condition; and (c) relieving the condition, i.e., causing its regression.

An "effective amount" is an amount sufficient to effect beneficial or desired results. An effective amount can be administered in one or more administrations. An effective amount corresponds with the quantity required to provide a desired average local concentration of a particular biologic agent, in accordance with its known efficacy, within the vascular lumen, vascular Wall, or other site, for the intended period of therapy. A dose may be determined by those skilled in the art by conducting preliminary animal studies and generating a dose response curve, as is known in the art. Maximum concentration in the dose response curve would be determined by the solubility of the compound in the solution and by toxicity to the animal model, as known in the art.

Any suitable and effective amount can be supported on one or more implants to constitute an individual "treatment" or "dose".

The effective amount further corresponds with the quantity required to provide a desired average local concentration of the particular biologic agent, in accordance with its known efficacy, in the region of insertion of a stent or other device, for the intended period of therapy. Due allowance can be made for losses due to urination or circulatory fluctuation due to physical activity, for example, from ten to ninety percent loss allowance could be made depending upon the individual patient and their routines.

The terms "individual," "subject," "host," and "patient," used interchangeably herein, refer to a mammal, including, but not limited to, humans, murines, simians, felines, canines, equines, bovines, mammalian farm animals, mammalian sport animals, and mammalian pets. Human subjects are of particular interest.

As used herein, the terms "determining", "assessing", "assaying", "measuring" and "detecting" refer to both quantitative and qualitative determinations and as such, the term "determining" is used interchangeably herein with "assaying," "measuring," and the like. Where a quantitative determination is intended, the phrase "determining an amount" and the like is used. Where either a qualitative or quantitative determination is intended, the phrase "determining a level of proliferation" or "detecting proliferation" is used.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

It must be noted that as used herein and in the appended claims, the singular forms "a," "and," and "the" include plural referents unless the context clearly dictates otherwise. Thus, for example, reference to "a biomarker" includes a plurality of such biomarkers and reference to "the sample" includes reference to one or more samples and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Moreover any positively recited element of the disclosure provides basis for a negative limitation to exclude that element from the claims.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides methods for the identification of drugs for use with drug-eluting coronary stents and other devices, e.g. for percutaneous coronary intervention, that inhibit restenosis, promote wound healing, and prevent thrombotic events. The long term success of a stenting procedure generally includes (1) the prevention of the initial vascular smooth muscle hyperplasia resulting from the wound to the vessel induced by stent insertion, (2) promotion of re-endothelialization to normalize the vessel morphology and function, and (3) inhibition of local inflammation to allow wound healing to occur. Many of the complications of the stenting procedure (e.g. need for target lesion revascularization and thrombotic events once patients are taken off blood thinners) are due predominantly to incomplete wound healing and re-endothelialization.

Conventional drugs delivered by stent, for example rapamycin, paclitaxel and everolimus, have been selected for their ability to inhibit the proliferative events involved in rapid neointimal hyperplasia without regard to other relevant biological events. Patients treated with stents coated with these drugs may have incomplete wound healing and are at risk for late restenosis and thrombotic events. Thus, there is a need for better anti-restenosis drugs.

The present invention provides methods to identify those drugs and provide stents coated with new drugs and drug combinations. The methods and stents of the invention are based on the identification of drugs that display a favorable combination of features (or biological activities of importance), defined as (1) inhibition of smooth muscle cell proliferation (2) little or no effect on endothelial cell proliferation (3) inhibition of matrix remodeling with promotion of wound healing, (4) no promotion of thrombosis, (5) promotion of vessel relaxation and (6) selected anti-inflammatory activities. Description of the desired features, and the corresponding markers (or readout parameters), which are used to measure these features are listed in Table 1.

TABLE 1

Desired biological activities of an anti-restenosis drugs.

| Parameter and cells | Desired Change | Biological Rationale |
|---|---|---|
| proliferation (SMC)* | decrease | prevent neointimal hyperplasia |
| proliferation (EC)* | none or increase | promote reendothelialization |
| uPAR (EC, SMC) | decrease | prevent migration and remodeling |

TABLE 1-continued

Desired biological activities of an anti-restenosis drugs.

| Parameter and cells | Desired Change | Biological Rationale |
| --- | --- | --- |
| $PGE_2$ (EC, monocytes) | increase or none | promotes relaxation and diagnostic of inhibition of e.g. $PGI_2$ expression |
| Thrombomodulin (EC, SMC) | increase | promotes anti-thrombotic environment |
| Tissue factor (EC, SMC) | decrease | promotes anti-thrombotic environment |
| CD40 (monocytes, EC) | decrease | reduces activation of cells by platelets and T cells |
| IP-10 (EC, HDF) | decrease | reduces SMC proliferation and promotes pro-angiogenic enviroment |
| MCP-1 (VEC, SMC) | none | reduces monocyte infiltration but can promote endothelial precursor recruitment and angiogenesis |
| collagen I (HDF) | increase or none | indicative of wound healing |
| VEGFR2 (EC) | increase or none | promotes angiogenic state of endothelium |
| PAI-1 (HDF, SMC) | decrease | reduce SMC proliferation and migration |
| IL-8 (SMC) | decrease or none | prevent local infiltration by granulocytes |
| M-CSF (EC, SMC) | decrease or none | promotes reendothelialization but can also cause monocyte activation/differentiation |
| TNF-α (monocytes) | increase | possible effects on cell proliferation and/or apoptosis |

*Proliferation under both growth factor-mediated and inflammatory conditions. EC, endothelial cell (either coronary artery or umbilical vein); SMC, smooth muscle cell (either coronary artery or umbilical artery), monocytes, peripheral blood monocyte; HDF, dermal fibroblast.

The BioMAP Systems that model the relevant biological processes (smooth muscle cell hyperplasia, tissue remodeling, inflammation etc, including the measurements of readout parameters listed in Table 1), and are used for screening are listed in Table 2. Each of the cells listed in Table 1 can be utilized in one or more of the systems described below. For example, smooth muscle cells are used in CASM3C; CASMNo; SM3C and SMNo systems. Such BioMap systems are generally primary human cell based assays. Compounds are screened in one or more such BioMap systems, usually in at least about two such systems, and may be screened in at least three, at least four, at least five, at least ten, and up to all of the assays set forth in Table 2.

In some embodiments of the invention, compounds are screened in at least one system utilizing smooth muscle cells, and at least one system utilizing endothelial cells. In some embodiments, the compounds are further screened in at least one system related to inflammation, for example systems LPS, 3C, 4H and HSM3C, which incorporate inflammatory cells (monocytes, T cells, endothelial cells) and mediators (TNF-α, IFN-γ etc.). In other embodiments, compounds are further screened in at least one system related to tissue remodeling, for example systems HDF3CT, HDFT and CASM3C, which incorporate cell types (fibroblasts, smooth muscle cells) and factors (e.g. growth factors) involved in tissue remodeling.

These assays are scored according to their modulation of the selected readout parameters. Compounds receive a score of positive (score of 1) or negative (score of 0) for each readout parameter set forth in Table 1 that is modulated. The compounds that score higher than a control compound, usually an approved therapeutic agent for inhibition of restenosis, e.g. rapamycin or paclitaxel, are considered an improvement over the approved therapeutic agent, and may be selected for further use.

TABLE 2

BioMAP Systems used to screen for anti-restenosis agents with desired features.

| System | Cell Types | Environment | Readout Parameters |
| --- | --- | --- | --- |
| 3C | Umbilical Vein Endothelial Cells | IL-1β + TNF-α + IFN-γ | MCP-1, uPAR, tissue factor, thrombomodulin, SRB*, Proliferation |
| HNo | Umbilical Vein Endothelial Cells | None | Proliferation |
| 4H | Umbilical Vein Endothelial Cells | IL-4 + histamine | VEGFRII, uPAR, SRB |
| LPS | Peripheral Blood Mononuclear Cells + Umbilical Vein Endothelial Cells | TLR4 | CD40, M-CSF, PGE2, TNF-α, SRB |
| CA3C | Coronary Artery Endothelial Cells | IL-1β + TNF-α + IFN-γ | MCP-1, CD141, CD142, IP-10, IL-8, tissue factor, thrombomodulin, SRB, Proliferation |
| CANo | Coronary Artery Endothelial Cells | None | Proliferation |
| CASM3C | Coronary Artery Smooth Muscle Cells | IL-1β + TNF-α + IFN-γ | MCP-1, uPAR, tissue factor, thrombomodulin, SRB, Proliferation |
| CASMNo | Coronary Artery Smooth Muscle Cells | None | Proliferation |
| SM3C | Umbilical Artery Smooth Muscle Cells | IL-1β + TNF-α + IFN-γ | MCP-1, CD141, CD142, IP-10, IL-8, SRB, Proliferation |

TABLE 2-continued

BioMAP Systems used to screen for anti-restenosis agents with desired features.

| System | Cell Types | Environment | Readout Parameters |
|---|---|---|---|
| SMNo | Umbilical Artery Smooth Muscle Cells | None | Proliferation |
| HSM3C | Umbilical Vein Endothelial Cells + Umbilical Artery Smooth Muscle cells | IL-1β + TNF-α + IFN-γ | CD40, uPAR, IP-10, tissue factor, thrombomodulin, M-CSF, SRB |
| HDF3CT | Fibroblasts | IL-1β + TNF-α + IFN-γ + TGF-β | Collagen I, IP-10 |
| HDFT | Fibroblasts | TGF-β | Collagen I, SRB, PAI-1 |

SRB, sulforhodamine B

The relative importance of each parameter may be weighted by the screener to select those parameters of greatest interest for a particular application. While a preferred drug modulates all of the readout parameters in the desired way; desirable bioactive compounds may also modulate only one or several of the parameters in the desired fashion. One can combine two or more drugs such that more of the desired parameter changes are obtained than either drug is capable of inducing alone. For restenosis, preferred compounds are those which have high overall score and which inhibit smooth muscle cell proliferation without affecting endothelial cell proliferation.

A library of over 1000 physiologically active compounds was screened in the assays listed in Table 2, for the activities listed in Table 1. Because of the importance of the inhibition the neointimal hyperplasia that occurs after stenting procedure, compounds that selectively inhibit smooth muscle cell proliferation versus endothelial cell proliferation were identified. The resulting compounds were evaluated and scored according to the activities listed in Table 2, receiving a 1 value for each activity present (Table 3). Overall scores of paclitaxel and rapamycin are shown for comparison. Thus, compounds that have overall scores equal or higher than paclitaxel and rapamycin, but at the same time differentially affect proliferation of smooth muscle and endothelial cells proliferation, are considered an improvement over the existing drugs for the treatment of restenosis. Among the compounds with high scores in the BioMAP screen (Table 4), esculetin has been reported to inhibit neointimal hyperplasia after balloon vascular injury in the rat (Pan et al., 2003), thus independently confirming the validity of the screening method described here.

TABLE 3

Parameter scores for selected drugs.

| | 3C | | | 4H | | | | LPS | | | | | CA3C | | | | | | | | CASM3C | | | | HDF3CT | |
|---|---|---|---|---|---|---|---|---|---|---|---|---|---|---|---|---|---|---|---|---|---|---|---|---|---|---|
| | MCP-1 | uPAR | GF Prolif. | Inflam. Prolif. | SRB | uPAR | SRB | VEGFR2 | CD40 | M-CSF | PGE2 | SRB | TNF-alpha | MCP-1 | TM | TF | IP-10 | IL-8 | GF Prolif. | Inflam. Prolif. | SRB | MCP-1 | uPAR | GF Prolif. | Inflam. Prolif. | SRB | IP-10 | Collagen I | SRB |
| Cis-(Z)-Flupentixol Dihydrochloride | 0 | 1 | 1 | 1 | 1 | 1 | 1 | 1 | 0 | 1 | 0 | 1 | 0 | 1 | 1 | 0 | 1 | 0 | 1 | 1 | 0 | 1 | 1 | 1 | 1 | 1 | 0 | 1 | 1 |
| Betulin | 1 | 0 | 1 | 1 | 1 | 0 | 1 | 1 | 0 | 1 | 0 | 1 | 1 | 0 | 1 | 0 | 1 | 1 | 0 | 0 | 0 | 1 | 0 | 1 | 1 | 1 | 0 | 1 | 1 |
| Chlorambucil | 1 | 0 | 1 | 1 | 1 | 1 | 1 | 0 | 1 | 0 | 0 | 1 | 0 | 1 | 0 | 1 | 0 | 1 | 1 | 1 | 1 | 1 | 0 | 1 | 1 | 1 | 0 | 1 | 1 |
| Trimethylcolchicinic Acid | 1 | 0 | 1 | 1 | 1 | 0 | 1 | 1 | 0 | 1 | 0 | 1 | 0 | 1 | 1 | 1 | 1 | 0 | 1 | 1 | 1 | 1 | 0 | 1 | 1 | 1 | 0 | 1 | 1 |
| B-Azaguanine | 0 | 1 | 0 | 0 | 1 | 0 | 1 | 0 | 0 | 1 | 0 | 1 | 0 | 0 | 1 | 0 | 1 | 1 | 0 | 1 | 1 | 1 | 1 | 1 | 1 | 1 | 0 | 1 | 1 |
| Nifedpine | 1 | 1 | 1 | 0 | 1 | 0 | 1 | 0 | 1 | 0 | 0 | 1 | 0 | 1 | 0 | 1 | 0 | 1 | 0 | 0 | 1 | 1 | 0 | 1 | 1 | 1 | 0 | 1 | 1 |
| Securinine | 1 | 0 | 1 | 1 | 1 | 0 | 1 | 0 | 0 | 0 | 0 | 1 | 0 | 1 | 0 | 0 | 1 | 0 | 1 | 1 | 1 | 1 | 0 | 1 | 1 | 1 | 1 | 1 | 1 |
| Primaquine Diphosphate | 1 | 0 | 1 | 1 | 1 | 10 | 1 | 1 | 1 | 1 | 0 | 1 | 0 | 1 | 0 | 0 | 0 | 0 | 0 | 0 | 1 | 1 | 0 | 1 | 1 | 1 | 0 | 1 | 1 |
| Deferoxamine Mesylate | 1 | 0 | 0 | 1 | 1 | 0 | 1 | 1 | 0 | 1 | 1 | 1 | 0 | 1 | 1 | 0 | 0 | 0 | 0 | 0 | 1 | 1 | 0 | 1 | 1 | 1 | 0 | 1 | 1 |
| Esculetin | 1 | 0 | 0 | 1 | 1 | 0 | 1 | 0 | 1 | 1 | 0 | 1 | 0 | 1 | 0 | 0 | 0 | 0 | 0 | 1 | 1 | 1 | 0 | 1 | 1 | 1 | 0 | 1 | 1 |
| Monobenzone | 1 | 0 | 0 | 0 | 1 | 1 | 1 | 0 | 0 | 0 | 0 | 1 | 0 | 1 | 0 | 0 | 0 | 0 | 1 | 1 | 1 | 1 | 0 | 1 | 1 | 1 | 0 | 1 | 1 |
| Amodiaquin Dihydrochloride Dihydrate | 1 | 0 | 0 | 0 | 1 | 0 | 1 | 1 | 0 | 1 | 0 | 1 | 0 | 1 | 0 | 0 | 0 | 0 | 0 | 0 | 1 | 1 | 0 | 1 | 1 | | 1 | | |
| Terconazole | 0 | 0 | 0 | 0 | 1 | 0 | 1 | 0 | 0 | 1 | 0 | 1 | 0 | 1 | 1 | 0 | 0 | 0 | 1 | 0 | 1 | 1 | 0 | 1 | 1 | 1 | 0 | 1 | 1 |
| Doxazosin Mesylate | 1 | 0 | 0 | 0 | 1 | 0 | 1 | 0 | 0 | 1 | 0 | 1 | 0 | 1 | 1 | 0 | 0 | 0 | 1 | 0 | 1 | 1 | 0 | 1 | 1 | 1 | 0 | 1 | 1 |
| Atovaquone | 0 | 1 | 0 | 0 | 1 | 0 | 1 | 0 | 0 | 0 | 0 | 1 | 0 | 1 | 0 | 0 | 0 | 0 | 0 | 1 | 1 | 1 | 0 | 1 | 1 | 1 | 0 | 0 | 1 |
| Syrosingopine | 1 | 0 | 0 | 0 | 1 | 0 | 1 | 0 | 0 | 1 | 0 | 1 | 0 | 1 | 1 | 0 | 0 | 0 | 1 | 0 | 1 | 1 | 0 | 1 | 1 | 1 | 0 | 1 | 1 |
| Clofilium Tosylate | 1 | 0 | 1 | 0 | 1 | 0 | 1 | 0 | 0 | 1 | 1 | 1 | 1 | 1 | 0 | 0 | 0 | 0 | 1 | 1 | 1 | 1 | 0 | 0 | 1 | 1 | 0 | 0 | 1 |
| Ciclopirox Ethanolamine | 0 | 0 | 0 | 0 | 1 | 0 | 1 | 0 | 0 | 1 | 0 | 1 | 0 | 1 | 0 | 0 | 0 | 0 | 0 | 0 | 1 | 0 | 0 | 1 | 1 | 1 | 0 | 0 | 0 |
| Paclitaxel | 1 | 1 | 0 | 0 | 1 | 0 | 1 | 1 | 0 | 1 | 0 | 1 | 0 | 1 | 0 | 0 | 0 | 0 | 0 | 0 | 1 | 1 | 0 | 1 | 1 | 1 | 1 | 1 | 1 |
| Rapamycin | 1 | 1 | 0 | 0 | 1 | 0 | 1 | 0 | 0 | 1 | 0 | 1 | 0 | 1 | 0 | 0 | 0 | 0 | 0 | 0 | 1 | 1 | 0 | 1 | 1 | 1 | 1 | 1 | 1 |

TABLE 3-continued

Parameter scores for selected drugs.

| | HDFT | | | | HSM3C | | | | | SM3C | | | | | | | Total Score |
|---|---|---|---|---|---|---|---|---|---|---|---|---|---|---|---|---|---|
| | Collagen I | PAI-1 | SRB | CD40 | uPAR | IP-10 | M-CSF | SRB | MCP-1 | TM | TF | IP-10 | IL-8 | GF Prolif. | Inflam. Prolif. | SRB | |
| Cis-(Z)-Flupentixol Dihydrochloride | 1 | 0 | 1 | 1 | 1 | 1 | 1 | 1 | 1 | 1 | 0 | 0 | 0 | 1 | 1 | 1 | 33 |
| Betulin | 1 | 0 | 1 | 1 | 0 | 1 | 1 | 1 | 1 | 1 | 0 | 0 | 1 | 1 | 1 | 1 | 31 |
| Chlorambucil | 1 | 0 | 1 | 1 | 0 | 1 | 1 | 1 | 1 | 0 | 0 | 1 | 0 | 1 | 1 | 1 | 30 |
| Trimethylcolchicinic Acid | 1 | 0 | 1 | 1 | 0 | 0 | 1 | 1 | 1 | 1 | 0 | 0 | 0 | 1 | 1 | 1 | 29 |
| B-Azaguanine | 1 | 0 | 1 | 1 | 0 | 1 | 1 | 1 | 1 | 0 | 0 | 1 | 0 | 1 | 1 | 1 | 28 |
| Nifedpine | 1 | 0 | 1 | 1 | 1 | 1 | 1 | 1 | 1 | 0 | 0 | 0 | 0 | 1 | 1 | 1 | 28 |
| Securinine | 1 | 1 | 1 | 0 | 0 | 0 | 1 | 1 | 1 | 0 | 0 | 1 | 0 | 1 | 1 | 1 | 28 |
| Primaquine Diphosphate | 1 | 0 | 1 | 0 | 0 | 1 | 1 | 1 | 1 | 0 | 0 | 0 | 0 | 1 | 1 | 1 | 27 |
| Deferoxamine Mesylate | 1 | 0 | 1 | 0 | 0 | 0 | 1 | 1 | 1 | 1 | 0 | 0 | 0 | 1 | 1 | 1 | 26 |
| Esculetin | 1 | 0 | 1 | 1 | 0 | 0 | 1 | 1 | 1 | 0 | 0 | 0 | 0 | 1 | 1 | 1 | 25 |
| Monobenzone | 1 | 0 | 1 | 0 | 0 | 0 | 1 | 1 | 1 | 0 | 0 | 0 | 0 | 1 | 1 | 1 | 24 |
| Amodiaquin Dihydrochloride Dihydrate | 1 | 0 | 1 | 0 | 0 | 1 | 1 | 1 | 1 | 0 | 0 | 0 | 0 | 1 | 1 | 1 | 23 |
| Terconazole | 1 | 0 | 1 | 0 | 0 | 0 | 1 | 1 | 1 | 0 | 0 | 0 | 0 | 1 | 1 | 1 | 22 |
| Doxazosin Mesylate | 1 | 0 | 1 | 0 | 0 | 0 | 1 | 1 | 1 | 0 | 0 | 0 | 0 | 1 | 0 | 1 | 22 |
| Atovaquone | 1 | 0 | 1 | 0 | 0 | 1 | 1 | 1 | 1 | 0 | 0 | 1 | 0 | 1 | 1 | 1 | 22 |
| Syrosingopine | 1 | 0 | 1 | 0 | 0 | 0 | 1 | 1 | 1 | 0 | 0 | 0 | 0 | 1 | 1 | 1 | 22 |
| Clofilium Tosylate | 1 | 0 | 1 | 0 | 0 | 0 | 1 | 1 | 1 | 0 | 0 | 0 | 0 | 0 | 1 | 1 | 22 |
| Ciclopirox Ethanolamine | 0 | 0 | 1 | 0 | 0 | 0 | 1 | 1 | 0 | 0 | 0 | 1 | 0 | 1 | 1 | 1 | 20 |
| Paclitaxel | 1 | 0 | 1 | 0 | 0 | 0 | 1 | 1 | 1 | 1 | 0 | 0 | 0 | 1 | 1 | 1 | 26 |
| Rapamycin | 1 | 0 | 1 | 0 | 0 | 0 | 1 | 1 | 1 | 0 | 0 | 0 | 0 | 1 | 1 | 1 | 24 |

TABLE 4

Total score for desired parameter modulation.

| Drug | Drug Class | Score (out of 45) |
|---|---|---|
| Cis-(Z)-Flupentixol Dihydrochloride | Dopamine receptor antagonist | 33 |
| Betulin | Natural product, antiviral | 31 |
| Chlorambucil | Alkylating agent | 30 |
| Trimethylcolchicinic Acid | Inactive colchicine analog | 29 |
| 8-Azaguanine | Purine antagonist, antiproliferative | 28 |
| Nifedipine | L-type calcium channel blocker | 28 |
| Securinine | GABA receptor antagonist | 28 |
| Primaquine Diphosphate | Anti-malarial | 27 |
| Deferoxamine Mesylate | Iron chelator | 26 |
| Esculetin | Lipoxygenase inhibitor | 25 |
| Monobenzene | Bleaching agent | 24 |
| Amodiaquin Dihydrochloride Dihydrate | Anti-malarial | 23 |
| Terconazole | Fungal cytochrome P-450 inhibitor | 22 |
| Doxazosin Mesylate | Alpha(1)-adrenoreceptor inhibitor | 22 |
| Atovaquone | Anti-malarial | 22 |
| Syrosingopine | Catecholamine depletion | 22 |
| Clofilium Tosylate | Potassium channel inhibitor | 22 |
| Ciclopirox Ethanolamine | Anti-fungal | 20 |
| Paclitaxel (average of 11 runs) | Tubulin binder | 26 ± 2 |
| Rapamycin (average of 13 runs) | mTOR inhibitor | 24 ± 1 |

Thus, in one embodiment, the present invention provides a stent or other device intended for in vivo use, wherein said stent or device comprises one or more drugs selected from the group consisting of 8-Azaguanine, Amodiaquin Dihydrochloride Dihydrate, Atovaquone, Betulin, Chlorambucil, Ciclopirox Ethanolamine, Cis-(Z)-Flupentixol Dihydrochloride, Clofilium Tosylate, Deferoxamine Mesylate, Doxazosin Mesylate, Esculetin, Monobenzone, Nifedipine, Primaquine Diphosphate, Securinine, Syrosingopine, Terconazole, and a colchicine analog, e.g. Trimethylcolchicinic Acid, where the preferred set of agents or drugs is selected from a group consisting of, Cis-(Z)-Flupentixol Dihydrochloride, Clofilium Tosylate, Monobenzone, Nifedipine, Primaquine Diphosphate, Securinine, and a colchicine analog, e.g. Trimethylcolchicinic Acid, and where the most preferred set of agents includes Trimethylcolchicinic Acid and its derivatives as further described below.

In another embodiment, the present invention provides a stent or other device intended for in vivo use, wherein said stent or device comprises one of the drugs selected from the group 8-Azaguanine, Amodiaquin Dihydrochloride Dihydrate, Atovaquone, Betulin, Chlorambucil, Ciclopirox Ethanolamine, Cis-(Z)-Flupentixol Dihydrochloride, Clofilium Tosylate, Deferoxamine Mesylate, Doxazosin Mesylate, Esculetin, Monobenzone, Nifedipine, Primaquine Diphosphate, Securinine, Syrosingopine, Terconazole, and a colchicine analog, e.g. Trimethylcolchicinic Acid in combination with a second biologically active agent. Such biologically active agents may include, without limitation, clinically proven anti-inflammatory such as a glucocorticoid receptor agonist (e.g. prednisolone, methylprednisolone, budesonide), a pro-healing drug (e.g. estradiol), a lipid metabolism modulating drug (e.g. statins), an anti-thrombotic drug etc.

Compounds of interest as a second agent may include chemotherapeutic agents for neoplastic tissues, anti-inflammatory agents for ischemic or inflamed tissues, hormones or hormone antagonists for endocrine tissues, ion channel modifiers for cardiovascular or other tissues, and neuroactive agents for the central nervous system. Exemplary of pharmaceutical agents suitable for this invention are those described in The Pharmacological Basis of Therapeutics, Goodman and Gilman, McGraw-Hill, New York, N.Y., (1993) under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Agents may be in the form of simple drugs, peptides, peptide fragments, DNA, RNA, ribozymes or engineered hybrids of nucleic acids and peptides or peptide fragments, or derivatives of each.

Specific agents of interest include therapeutic agents that inhibit in-stent restenosis. Such agents may include rapamycin; antiplatelet agents; GPIIb/IIIa inhibitors, e.g. RheoPro; DNA; ribozymes; RNA; antiplatelet drugs, e.g. aspirin and dipyridamole; anticoagulant drugs, including heparin, coumadin, protamine, and hirudin; antimitotics (cytotoxic agents) that work directly to prevent cell mitosis (replication) and antimetabolites that prevent replication, e.g. methotrexate, colchicine, azathioprine, vincristine, vinblastine, fluorouracil, adriamycin, mutamycin, etc. Anti-inflammatory drugs such as glucocorticoids, e.g. dexamethasone, betamethasone, etc. can also be useful to locally suppress inflammation caused by injury to luminal tissue during angioplasty.

Angiotensin converting enzyme inhibitors (ACE-I) are used for antihypertensive and renoprotective actions. ACE inhibitor include, but are not limited to, captopril, benazepril, enalapril, fosinopril, lisinopril, quinapril, Ramipril, imidapril, perindopril, erbumine, and trandolapril. ACE receptor blockers may also be used in place of or as well as ACE inhibitors, and these include losartan, irbesartan, candesartan, cilexetil, and valsartan.

Nicotine receptor agonist, e.g. nicotine (S-3-(1-methyl-2-pyrrolidinyl)pyridine) and other compounds that substantially specifically bind a nicotine receptor and provide a pharmacological effect. "Nicotine receptor agonists" encompass naturally-occurring compounds (including, but not limited to, small molecules, polypeptides, peptides, etc., particularly naturally-occurring plant alkaloids, and the like), endogenous ligands (e.g., purified from a natural source, recombinantly produced, or synthetic, and further including derivatives and variants of such endogenous ligands), and synthetically produced compounds (e.g., small molecules, peptides, etc.) The term "nicotine" further includes any pharmacologically acceptable derivative or metabolite of nicotine which exhibits pharmacotherapeutic properties similar to nicotine. Such derivatives, metabolites, and derivatives of metabolites are known in the art, and include, but are not necessarily limited to, cotinine, norcotinine, nornicotine, nicotine N-oxide, cotinine N-oxide, 3-hydroxycotinine and 5-hydroxycotinine or pharmaceutically acceptable salts thereof.

Agents that increase nitric oxide are of interest as anti-restonic agents, e.g. S-nitrosopenicillamine, sodium nitroprusside, N-ethyl-2-(1-ethyl-2-hydroxy-2-nitrosohydrazino) ethanamine (NOC 12), etc. The production of nitric oxide may also be modulated by cytokines, such as γ-interferon, tumor necrosis factor, IL-1, IL-2 and endotoxin due to their effect on the enzyme, nitric oxide synthase. The inducible form of NO synthase is increased by cytokines and the constitutive form seems to be decreased by cytokines. HMG-CoA reductase inhibitors have been found to upregulate endothelial cell NOS activity, as described by U.S. Pat. No. 6,147,109, Liao et al., Any of the forms of nitric oxide synthase can be utilized, as the protein or an active fragment derived therefrom, or as a DNA construct for expression.

Also of interest for the inhibition of restenosis are compounds with an anti-angiogenic effect. These include the anti-angiogenic polypeptides: angiostatin (O'Reilly et al. (1994) Cell 79:315-328); endostatin (O'Reilly et al. (1997) Cell 88: 277-285); and anti-angiogenic anti-thrombin III (Bock et al. (1982) Nucleic Acids Res. 10 (24), 8113-8125); and the like, and further include functionally active variants and derivatives thereof. Other anti-angiogenic agents include inhibitors of matrix metalloproteases, e.g. amifostine, WR-1065; marimastat, primomastat, alpha-1 antitrypsin; and the like.

Alternatively, compounds that block thrombin, and other anti-coagulants, may be used to inhibit restenosis, such compounds based on the tripeptide motif D-Phe-Pro-Arg; e.g. LY287045, etc. Many compounds, such as inogatran and melagatran, are known in the art. For non-limiting examples, see U.S. Pat. Nos. 6,326,386; 6,232,315; 6,201,006; 6,174,855; 6,060,451; and 5,985,833; among others.

Agonists of the TGF-beta receptor are also of interest. TGF-β receptor Type I and type II mediate most activities of TGF-beta (Ebner et at. (1993) *Science* 260:1344-1348; and Franzen et al. (1993) *Cell* 75: 681-692). Ligands include TGF-β, and mimetics and biologically active derivatives thereof.

Complex systems of drugs may be carried by the prosthesis, i.e. stent or other device. An anticoagulant or antiplatelet may be included in the outermost surface of the device in order to elute off very quickly for the first several days. Antiinflammatories and antireplicates can be formulated into the device to continue to elute later, when in contact with non-blood cells after neointima overgrowth has surrounded the device. The drug elution rate does not need to be uniform, and may be tailored to fit the need of the patient.

As used herein, the term stent is used as is known in the art, to refer to a prosthesis which can be inserted and held, when desired, in a lumen of a vessel or organ in the body. Uses include the support of blood vessels, the trachea, renal and urethral tubules, fallopian tubes, eustachian, large and small intestines, etc. Materials commonly used in stent construction include biologically compatible metals, e.g. stainless steel, titanium, tantalum, gold, platinum, copper and the like, as well as alloys of these metals; low shape memory plastic; a shape-memory plastic or alloy, such as nitinol; and the like. Any of these materials can be fabricated to form channels for use in the present invention, and can form, or be derivatized to form, covalent bonds with the matrix.

There are a multiplicity of different stents that may be utilized. Although any number of stents may be utilized in accordance with the present invention, for simplicity, several representative stents will be described in exemplary embodiments of the present invention. The skilled artisan will recognize that any kind of stent may be utilized in connection with the present invention. Non-limiting examples of commercially available stents include the Gianturco-Roubin stent and the Palmaz-Schatz stent, commonly used for tandem short segment stenotic lesions; Wallstent (Boston Scientific, Natick, Mass.), a self expanding stainless stent used for long lesions; Mammotherm stent, Symphony stent, Smart stent, all of self expanding nitinol; the balloon exapandable Perflex, AVE, Intrastent, and Herculink stents, self-expanding Instent, Gianturco Z-stent (Wilson-Cook, Winston-Salem, N.C.), Ultraflex nitinol mesh stent (Microinvasive, Natick, Mass.), and Esophacoil (IntraTherapeutics, Eden Prairie, Minn.). Tracheobronchial stents include the Gianturco Z tracheobronchial tree stent and the Wallstent tracheobronchial endoprosthesis. The stent may be self-expanding, or may be expandable with a balloon, as is known in the art.

Additional platforms for the invention include polymeric biodegradable stents, anastomotic devices, and scaffolds, including synthetic biodegradable or bioerodible porous scaffolds produced using solid free-form fabrication techniques which include selective laser sintering, three-dimensional printing, fused deposition manufacturing, and stereolithography for micro- or nano-fabrication.

In one embodiment of the invention, the drug or drugs are formulated as a liquid for release from a stent. For example, a stent may include a chamber with a drug transport wall, where the anti-restenotic agent is loaded into the chamber, then selectively transported through the wall (see U.S. Pat. No. 5,498,238). Other variations of this approach include the use of a hollow tubular wire stent, or a stent comprising a reservoir. Such stents are described in the art as having side walls facing outwardly having holes for delivery of the liquid formulation to the targeted site, where the stent is implanted (U.S. Pat. No. 5,891,108). The anti-restenotic agent may be diffused from a reservoir directly to the walls of a blood vessel, through directional delivery openings arranged on an outer surface of the stent. Such devices may also comprise an osmotic engine assembly for controlling the delivery of the agent from the reservoir (U.S. Pat. No. 6,071,305).

An alternative to liquid formulation is provided by devices that comprise a drug compounded to the device itself. In one embodiment, the stent itself is formed of a polymeric material comprising the anti-restenotic agent, where the stent is biodegradable or bioabsorbable (see U.S. Pat. No. 6,004,346). Alternatively, the prostheses may be biostable in which case the drug is diffused out from the biostable materials in which it is incorporated. With metal stents, the device can include a drug-carrying coating overlying at least a portion of the metal.

Alternatively the device may comprise a drug carrying coating. For example a porous stent can be made from a powdered metal or polymer, where the anti-restenotic agents are then compressed into the pores of the stent (see U.S. Pat. Nos. 5,972,027; and 6,273,913). Stents for drug delivery can also comprise multiple coatings, where the rate of release is different for the two coatings (see U.S. Pat. No. 6,258,121), where one of the anti-restenotic agents can be present in both coatings to provide for an extended release profile; or where two or more anti-restenotic agents are differentially released. Other composite coatings include at least one composite layer of the anti-restenotic agent and a polymer material, and at least a barrier layer positioned over the composite layer and being of thickness adequate to provide a controlled release of the bioactive agent (see U.S. Pat. No. 6,335,029). The sheath over the coating containing the anti-restenotic agent can also be perforated, so that when the stent is compressed, the perforation is closed. Upon placement in the vessel, the stent is expanded, and the perforation is opened (see U.S. Pat. No. 6,280,411).

Drugs may be held by covalent bonds (eg, C—C bonds, sulfur bridges) or noncovalent bonds (eg, ionic, hydrogen bonds). The blended matrix may then be attached to the stent surface by dipping or spraying the stent, or other coating methods known in the art. The drug can alternatively be encapsulated in microparticles or nanoparticles and dispersed in a stent coating. A diffusion limiting top-coat may optionally be applied to the above coatings. Drugs may also be released by particle dissolution or diffusion when nonbioerodable matrices are used, or during polymer breakdown when incorporated (absorbed) into a biodegradable substance.

In some embodiments, a drug delivery device which is distinct from the stent may be implanted proximally to the site of stent insertion to effect the long-term release of a drug. Without limitation, such drug delivery devices may include biodegradable microparticles injected into, or coated so as to adhere to, the vascular wall; sheets of material fabricated from biodegradable hydrogels (i.e., gelatin, alginate), ethylene vinyl acetate, chitosan, silk fibroin, poly(D,L-lactide-co-glycolide), poly-L-lactide-co-caprolactone, poly(hydroxyvalerate), poly (L-lactic acid), poly(D,L-lactic acid), poly (glycolic acid), polycaprolactone, polyanhydride, polydiaxanone, polyorthoester, polyamino acids, poly(trimethylene carbonate), peptide nanofibers or other or other suitable synthetic polymers as sheets, particles, rings, or other convenient geometries. As discussed above, drugs may be released by particle dissolution or diffusion when nonbioerodable matrices are used, or during polymer breakdown when incorporated (absorbed) into a biodegradable substance.

The screening methods of the invention are practiced by assaying a test agent for its ability to affect a number of biological activities that are positively or negatively correlated with the ability of drugs to inhibit restenosis. These biological activities are indicative of whether the agent can affect (1) selected inflammatory responses (which selected activities may include T cell responses, endothelial and smooth muscle cell responses, production of chemokines), (2) cell proliferation, for example of smooth muscle cells and/or endothelial cells, (3) tissue remodeling (expression of proteins involved in matrix production and degradation: collagen 1, uPAR, PAI-1), (4) vasorelaxation (PGE2 levels) and (5) thrombosis (expression of proteins involved in thrombosis: tissue factor, thrombomodulin). Preferred agents for preventing restenosis inhibit smooth muscle proliferation with little or no effect on endothelial cell proliferation, inhibit matrix remodeling, is vasorelaxant, is not pro-thrombotic, and induces select anti-inflammatory activities.

While any method for assaying one of the biological activities of interest can be used in the present method, BioMAP Systems are the most informative and efficient to use in the method. The BioMAP Systems included assays utilizing endothelial cells, smooth muscle cells, monocytes, T cells, and fibroblasts, and the assays were conducted to assess the impact of these agents on cell proliferation (smooth muscle and endothelial cell) and on markers of tissue remodeling, inflammation, and thrombosis.

In general, BioMAP Systems are designed to model complex human disease biology in a practical in vitro format. This is achieved by stimulating human primary cells (single cell type or defined mixtures of cell types) such that multiple disease-relevant signaling pathways are simultaneously active. The choice of cell types and stimulations is guided by the knowledge of disease biology and mechanisms. Incorporating appropriate cell types and stimulating signaling pathways relevant to disease states allows association of biological activities detected in BioMAP Systems with disease processes. Drug effects are then recorded by measuring biologically meaningful protein readouts that provide coverage of biological space of interest (e.g., inflammation, tissue remodeling) and allow discrimination between different drug classes tested. The BioMAP systems useful for this evaluation are listed in Table 2.

Without being limited to the theory, some of the rationale for inclusion of certain parameters is outlined below. The successful stent drugs paclitaxel, rapamycin and everolimus are potent inhibitors of smooth muscle cell proliferation, suggesting that this is a required biological effect in order to prevent restenosis. These compounds are also potent inhibitors of endothelial cell proliferation and therefore would prevent wound healing, which activity is desirably avoided.

Cell migration and matrix remodeling processes are regulated by certain proteins such as uPAR and PAI-1, and play important roles in neointima formation (Behrendt, 2004; Stefansson, 2003). High levels of uPA are a risk factor for restenosis (Strauss, 1999). $PGE_2$ and other prostaglandin pathway components (e.g. $PGI_2$) that upregulate cAMP are known smooth muscle cell relaxants and growth inhibitors (Wong, 2001). Inflammation plays a key role in atherosclerosis, and inflammatory markers, including MCP-1 and CD40, are increased in patients (Garlichs, 2001; Deo, 2004). High pre-angioplasy levels of the inflammatory protein CD40L (the ligand for CD40) are predictive of higher restenosis rates after angioplasty (Cipollone et al., 2003; L'Allier, 2005). Other chemokines such as IL-8 and IP-10 will positively and negatively regulate angiogenesis, respectively (Belperio, 2000) as well as being involved in the recruitment of inflammatory leukocytes. Collagen I production is associated with the resolution of wound healing. VEGFR2 is the main VEGF receptor on angiogenic endothelium mediating migration and proliferation, suggesting that promotion of expression of this receptor is desired (Rahimi, 2000). M-CSF is involved in differentiation of macrophages from monocytes as well as being a promoter of VEGF production and potentially reendothelialization (Eubank, 2003). The two approved stent drugs (paclitaxel and rapamycin) increase the level of TNF-α produced by monocytes as previously reported (Allen, 1993). Increases in TNF-α may induce other factors like prostaglandins to relax the smooth muscle, and inhibition of TNF-α has shown to worsen congestive heart failure patients (Chung, 2003), indicating that some level of TNF-α is protective. Preventing local thrombus formation may modulate the processes of wound healing and re-endothelialization, so that reductions in tissue factor and increases in thrombomodulin are important.

The method of the invention can be practiced with assays to assess the effect of an agent on the four key biological activities (cell proliferation, inflammation, thrombosis, and tissue remodeling), but because BioMAP Systems utilize co-cultures of different primary cell types as well as complex stimulation conditions with multiple disease-relevant factors, the present invention also provides additional embodiments that provide more information regarding an agent's utility in the inhibition of restenosis. Such additional assays include assays that reveal interactions of endothelial cells and monocytes/macrophages, effects of inflammatory factors on proliferation of smooth muscle and endothelial cells, differential effects of various growth factors stimuli on proliferation of smooth muscle and endothelial cells under inflammatory conditions, and additional readouts (e.g extracellular matrix).

The methods of the present invention are directed to the identification of novel anti-restenosis drugs. Agents suitable for testing in the method include, without limitation small molecular compounds, natural products, proteins peptides, plant or other extracts, in general any agent or substance with biological activity. In one embodiment, the invention is practiced to identify combinations of two or more agents that prevent restenosis.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, nucleic acids, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In another embodiment, the invention is practiced by additionally examining the effect on these biological activities of known drugs (including but not limited to anti-platelet drugs, statin drugs, and anti-hypertensive drugs) and then selecting the agent(s) for preventing restenosis on the basis of their complementarity of action with those drugs. Evaluation of drug combinations is useful, as patients receiving paclitaxel-coated stents are frequently prescribed other medications including statins and various anti-hypertensive drugs. Identifcation of particular drugs (or drug classes) that together with a known anti-restenosis agent, such as paclitaxel, provides enhanced anti-restenotic activities, without unexpected adverse activities, would provide optimal patient benefit. The methods of the invention are ideal for identifying synergistic activities, and the BioMAP systems exemplified detect the activity of an agent on a wide variety of biological mechanisms relevant to restenosis.

The present invention identifies drugs and provides stents coated with such drugs and drug combinations, where the drugs provide for a favorable combination of features (or biological activities of importance), defined as (1) inhibition of smooth muscle cell proliferation (2) little or no effect on endothelial cell proliferation (3) inhibition of matrix remodeling with promotion of wound healing, (4) no promotion of thrombosis, (5) promotion of vessel relaxation and (6) selected anti-inflammatory activities.

One can further refine the selection of drugs for the treatment of restenosis by measuring their relative effects at multiple doses on proliferation of smooth muscle cells and endothelial cells derived from different sources (umbilical cord or coronary artery), and under different growth conditions (proliferation driven by growth factors only, or in the presence of pro-inflammatory factors that are normally found at the restenotic site). Statistical analysis of cell proliferation in BioMAP systems 3C, SM3C, CANo, CASMNO, CA3C, and CASM3C listed in Table 1 was performed for candidate drugs 8-Azaguanine, Amodiaquin Dihydrochloride Dihydrate, Atovaquone, Ciclopirox, Cis-(Z)-Flupentixol Dihydrochloride, Clofilium Tosylate, Monobenzone, Primaquine Diphosphate, Securinine, Syrosingopine, Terconazole, and Trimethylcolchicinic Acid. Table 5 below shows the log ratios of smooth muscle cell to endothelial cell proliferation for the compounds. Drugs showing a ratio of >1 preferentially inhibit smooth muscle cell proliferation relative to endothelial cell proliferation and are especially promising candidates as inhibitors of restenosis (cells with no ratio means that both values of proliferation were not significantly different from DMSO control).

This analysis singles out Trimethylcolchicinic Acid (a colchicine analog) as promising because it shows preferential effect on smooth muscle cells over endothelial cells under all conditions, at all doses tested and independent of the source of primary cells.

Thus, in one embodiment, the present invention provides a stent or other device intended for in vivo use, wherein said stent or device comprises one or more colchicine analogs and their pharmaceutically acceptable salt as an active agent, where the agent has the structure I:

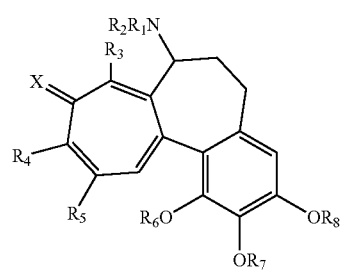

In another embodiment, the present invention provides a stent or other device intended for in vivo use, wherein said stent or device comprises one or more isocolchicine analogs and their pharmaceutically acceptable salt as an active agent, where the agent has the structure II:

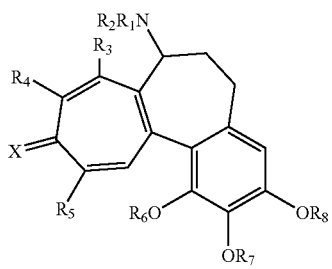

In structures I and II $R_1$ and $R_2$ are independently selected from H; $C_{1-10}$ alkyl, alkenyl, and alkynyl. $R_1$ and $R_2$ may also form a cycle containing between 1-6 carbon atoms provided that the cycle thus formed does not contain an alkynyl group. The alkyl, alkenyl and alkynyl groups can be optionally substituted with one or more of OH, $OR_9$, $NR_{10}R_{11}$ and F where $R_9$, $R_{10}$ and $R_{11}$, are independently chosen from branched and unbranched $C_{1-5}$ alkyl, provided that the OH and F substituents are not attached to the same carbon atom as is N in the structure above, that any F substituents are not allylic or propargylic, and that OH and $OR_9$ are not attached to the same carbon nor are OH and $NR_{10}R_{11}$ attached to the same carbon atom.

$R_3$ is selected from H, branched and unbranched $C_{1-6}$ alkyl, alkenyl and alkynyl.

X is O or $NOR_9$.

$R_4$ and $R_5$ are selected independently from H, OH, $OR_9$, $NR_1R_2$, provided that $R_9$ is not $CH_3$ when incorporated into $R_4$ when the structure is I.

Each of $R_6$, $R_7$ and $R_8$ are independently selected from branched or unbranched $C_{1-6}$ lower alkyl and $R_6$ and $R_7$ or $R_7$ and $R_8$ may form cycles containing 1 or 2 carbon atoms in the ring.

In one embodiment of the invention, the agent is compound III or a pharmaceutically acceptable salt thereof.

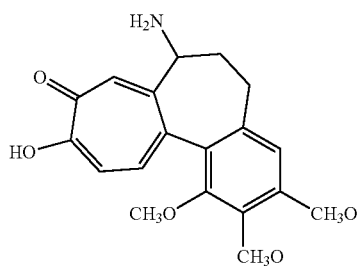

In another embodiment, the present invention provides a stent or other device intended for in vivo use, wherein said stent or device comprises a colchicine analog as set forth herein, in combination with a second biologically active agent. Such biologically active agents may include, without limitation, clinically proven anti-inflammatory such as a glucocorticoid receptor agonist (e.g. prednisolone, methylprednisolone, budesonide), a pro-healing drug (e.g. estradiol), a lipid metabolism modulating drug (e.g. statins), an antithrombotic drug etc.

Such stents and devices find use as is known in the art for the treatment or prevention of restenosis. For example, a stent may be into the vasculature of a patient following balloon angioplasty, where the stent or a device implanted proximally to the stent is designed to release one or more drugs according, to description set forth above, to delay or prevent the onset of restenosis. In such an embodiment, the colchicine analog is delivered at an effective local concentration of about 0.01 to about 100 μM. In some embodiments, the apparatus is configured so as to release the drugs for at least a portion of the intended duration of stent implantation, from 1 to about 60 days.

EXAMPLES

Cell Culture.

Human umbilical vein endothelial cells (HUVEC) were pooled from multiple donors, cultured according to standard methods, and plated into microtiter plates at passage 4. Human neonatal foreskin fibroblasts (HDF) from 3 donors were pooled and cultured according to standard methods. 24 hr before stimulation with cytokines, confluent HDF in microtitre plates were serum starved. Coronary artery endothelial cells (CAEC), coronary artery smooth muscle cells (CASMC) and umbilical artery smooth muscle cells (SMC) cultured according to standard methods. Peripheral blood mononuclear cells (PBMC) were prepared from buffy coats from normal human donors according to standard methods. Concentrations/amounts of agents added to confluent microtitre plates to build each system were as follows: cytokines (IL-1 beta, 1 ng/ml; TNF-alpha, 5 ng/ml; IFN-gamma, 20 ng/ml; TGF-beta, 5 ng/ml; IL-4, 5 ng/ml), activators (histamine, 10 microM; SAg, 20 ng/ml or LPS, 0.2 ng/ml), PBMC ($7.5 \times 10^4$ cells/well).

Compounds.

Compounds were prepared in the solvent as directed, added 1 hr before stimulation of the cells, and were present during the 24 hr stimulation period for the measurement of parameters listed in Table 2. For proliferation, compounds added 1 hr before stimulation of the cells with cytokines, and were present during the 96 hr. If prepared in DMSO, the final concentration of solvent was 0.1% or less.

Readout Parameter Measurements.

The levels of readout parameters were measured by ELISA. Briefly, microtiter plates are treated, blocked, and then incubated with primary antibodies or isotype control antibodies (0.01-0.5 microg/ml) for 1 hr. After washing, plates were incubated with a peroxidase-conjugated anti-mouse IgG secondary antibody or a biotin-conjugated anti-mouse IgG antibody for 1 hr followed by streptavidin-HRP for 30 min. Plates were washed and developed with TMB substrate and the absorbance (OD) was read at 450 nm (subtracting the background absorbance at 650 nm). Quantitation of TNF-alpha in the LPS system was done using a commercially available kit according to the manufacturer's directions. Proliferation of endothelial cells (HUVEC and CAEC), smooth muscle cels (SMC and CASMC), and PBMC (T cells) was quantitated by Alamar blue or SRB reduction.

Toxicity Assessments.

Adverse effects of compounds on cells were determined by (1) measuring alterations in total protein (Sulforodhamine B or SRB assay); (2) measuring the viability of peripheral blood mononuclear cells (incorporation of propidium iodide, PI); and (3) microscopic visualization. SRB was performed by staining cells with 0.1% sulforhodamine B after fixation with 10% TCA, and reading wells at 560 nm. PBMC viability was assessed by adding propidium iodide (10 microgram/ml) to PBMC that had been cultured for 24 hours in the presence of activators and measuring the percentage of cells that incorporated dye by flow cytometry after 10 minutes. Samples were assessed visually according to the following scheme:

2.0=cobblestone (unactivated phenotype); 1.0=activated (normal phenotype); 0.5=lacy or sparse; 0.375=rounded; 0.25=sparse and granular; 0.1=no cells in well.

Data Analysis.

Mean OD values for each parameter were calculated from triplicate samples per experiment. The mean value obtained for each parameter in a treated sample was then divided by the mean value from an appropriate control to generate a ratio. All ratios were then $\log_{10}$ transformed. 99% prediction envelopes (grey shading in Figures) were calculated for historical controls. Mean values+/−SD are shown.

Cellular toxicity in BioMAP Systems is indicated if the SRB parameter (sulforhodamine B, measure of total protein loss) is <−0.3, the PI parameter (propidium iodine, measure of lymphotoxicity) is <−0.1, and the Visual parameter (change in cell morphology) is <−0.6. Paclitaxel, rapamycin and dexamethasone showed no signs of toxicity at tested doses, and were active over the entire dose range. 17beta-estradiol and Actinomycin D showed signs of cellular toxicity at 10 microM and 4.572 nM, and were inactive at doses lower that 3.3 microM and 0.5 nM, respectively.

Statistical analysis of cell proliferation in the systems listed in Table 1 was performed for candidate drugs. Table 5 shows the log ratios of smooth muscle cell to endothelial cell proliferation for a subset of compounds including the highly promising compound Trimethylcolchicinic Acid. Drugs showing a ratio of >1 (green) preferentially inhibit smooth muscle cell proliferation relative to endothelial cell proliferation and are especially promising candidates as inhibitors of restenosis (cells with no ratio means that both values of proliferation were not significantly different from DMSO control).

Log ratios of proliferation in endothelial and smooth muscle cell model systems for selected compounds.

| Drug | Concentration | 3C HUEVEC | 3C SMC | Ratio | None CAEC | None CASMC | Ratio | 3C CAEC | 3C CASMC | Ratio |
|---|---|---|---|---|---|---|---|---|---|---|
| 8-Azaguanine | 33000 nM | −0.3 | −0.2 | 0.7 | −0.2 | −0.1 | 0.9 | −0.2 | −0.2 | 0.8 |
| 8-Azaguanine | 11000 nM | −0.3 | −0.1 | 0.5 | −0.1 | −0.1 | 1.1 | −0.2 | −0.1 | 0.6 |
| 8-Azaguanine | 3666.667 nM | −0.2 | −0.1 | 0.4 | −0.1 | −0.1 | 1.7 | 0.0 | 0.0 | |
| 8-Azaguanine | 1222.222 nM | 0.0 | 0.0 | | 0.0 | −0.1 | 98.0 | 0.0 | 0.0 | |
| Amodiaquin Dihydrochloride Dihydrate | 33000 nM | −0.8 | −0.1 | 0.2 | −0.3 | −0.3 | 1.1 | −0.6 | −0.3 | 0.4 |
| Amodiaquin Dihydrochloride Dihydrate | 11000 nM | −0.3 | −0.1 | 0.3 | 0.0 | −0.1 | 3.5 | −0.1 | −0.1 | 1.1 |
| Amodiaquin Dihydrochloride Dihydrate | 3666.667 nM | −0.1 | 0.0 | 0.4 | 0.0 | −0.1 | 4.4 | −0.1 | −0.1 | 1.1 |
| Amodiaquin Dihydrochloride Dihydrate | 1222.222 nM | 0.0 | 0.0 | | 0.0 | 0.0 | | 0.0 | 0.0 | |
| Atovaquone | 40000 nM | | −0.2 | 0.0 | −0.2 | −0.2 | 1.1 | −0.3 | −0.2 | 0.7 |
| Atovaquone | 13333.333 nM | −0.3 | 0.0 | | 0.0 | −0.1 | 1.7 | 0.0 | −0.1 | 7.6 |
| Atovaquone | 4444.444 nM | 0.0 | 0.0 | | 0.0 | −0.1 | 1.5 | 0.0 | 0.0 | |
| Atovaquone | 1481.481 nM | 0.0 | 0.0 | | 0.0 | 0.0 | | 0.0 | 0.0 | |
| Ciclopirox Ethanolamine | 55000 nM | −0.5 | −0.4 | 0.8 | −0.6 | −0.5 | 0.8 | −0.6 | −0.5 | 0.9 |
| Ciclopirox Ethanolamine | 18333.333 nM | −0.3 | −0.4 | 1.4 | −0.4 | −0.4 | 1.0 | −0.4 | −0.5 | 1.1 |
| Ciclopirox Ethanolamine | 6111.111 nM | −0.1 | −0.3 | 2.5 | −0.2 | −0.3 | 1.5 | −0.2 | −0.3 | 1.3 |
| Ciclopirox Ethanolamine | 2037.037 nM | −0.1 | −0.1 | 1.0 | 0.0 | 0.0 | | 0.1 | −0.1 | 1.5 |
| Cis-(Z)-Flupentixol Dihydrochloride | 30000 nM | −0.7 | −1.3 | 1.7 | −1.2 | −1.0 | 0.9 | −1.2 | −0.1 | 0.9 |
| Cis-(Z)-Flupentixol Dihydrochloride | 10000 nM | −1.0 | −0.4 | 0.4 | −0.3 | −0.6 | 1.9 | −0.9 | −0.8 | 0.9 |
| Cis-(Z)-Flupentixol Dihydrochloride | 3333.333 nM | −0.2 | 0.0 | 0.2 | 0.0 | 0.0 | | −0.1 | −0.1 | 0.8 |
| Cis-(Z)-Flupentixol Dihydrochloride | 1111.111 nM | −0.1 | 0.0 | 0.1 | 0.0 | 0.0 | | 0.0 | 0.0 | |
| Clofilium Tosylate | 30000 nM | −1.0 | −1.3 | 1.3 | −0.1 | −0.8 | 6.5 | −0.5 | −1.1 | 2.3 |
| Clofilium Tosylate | 10000 nM | −0.1 | −0.3 | 1.8 | 0.0 | −0.1 | 16.0 | 0.0 | −0.5 | 20.9 |
| Clofilium Tosylate | 3333.333 nM | 0.0 | 0.0 | | 0.0 | 0.0 | | 0.1 | 0.0 | |
| Clofilium Tosylate | 1111.111 nM | 0.0 | 0.0 | | 0.0 | 0.0 | | 0.0 | 0.0 | |
| Evelolimus | 370.37 nM | −0.3 | −0.2 | 0.6 | −0.3 | −0.2 | 0.6 | −0.3 | −0.2 | 0.6 |
| Evelolimus | 123.457 nM | −0.3 | −0.1 | 0.5 | −0.3 | −0.2 | 0.6 | −0.3 | −0.2 | 0.6 |
| Evelolimus | 41.152 nM | −0.3 | −0.1 | 0.5 | −0.3 | −0.2 | 0.6 | −0.3 | −0.2 | 0.7 |
| Evelolimus | 13.717 nM | −0.2 | −0.1 | 0.4 | −0.3 | −0.1 | 0.4 | −0.2 | −0.1 | 0.6 |
| Monobenzone | 75000 nM | −0.3 | −0.2 | 0.6 | −0.4 | −0.2 | 0.4 | −0.3 | −0.2 | 0.6 |
| Monobenzone | 25000 nM | −0.2 | −0.2 | 1.0 | −0.1 | −0.1 | 2.2 | −0.1 | −0.2 | 1.3 |
| Monobenzone | 8333.333 nM | 0.0 | −0.1 | 8.5 | 0.0 | 0.0 | | 0.0 | −0.1 | 7.4 |
| Monobenzone | 2777.778 nM | 0.0 | 0.0 | | 0.0 | 0.0 | | 0.0 | 0.0 | |
| Primaquine Diphosphate | 33000 nM | −0.3 | 0.0 | 0.1 | −0.1 | −0.1 | 0.9 | −0.3 | −0.2 | 0.9 |
| Primaquine Diphosphate | 11000 nM | −0.1 | 0.0 | 0.4 | 0.0 | 0.0 | | −0.1 | −0.1 | 0.4 |
| Primaquine Diphosphate | 3666.667 nM | 0.0 | 0.0 | | 0.0 | 0.0 | | −0.1 | 0.0 | 0.4 |
| Primaquine Diphosphate | 1222.222 nM | 0.0 | 0.0 | | 0.0 | 0.0 | | 0.0 | 0.0 | |
| Securinine | 44000 nM | −0.4 | −0.5 | 1.2 | −0.5 | −0.4 | 0.9 | −0.6 | −0.5 | 0.9 |
| Securinine | 14666.667 nM | −0.3 | −0.2 | 0.8 | −0.1 | −0.2 | 2.2 | −0.2 | −0.3 | 1.3 |
| Securinine | 4888.889 nM | −0.1 | −0.1 | 0.8 | 0.0 | −0.1 | 2.7 | −0.1 | −0.1 | 1.3 |
| Securinine | 1629.63 nM | 0.0 | 0.0 | | 0.0 | 0.0 | | 0.0 | −0.1 | 1.6 |
| Syrosingopine | 22222.222 nM | −0.7 | −0.3 | 0.5 | −0.3 | −0.6 | 1.7 | −0.5 | −0.7 | 1.3 |
| Syrosingopine | 7407.407 nM | −0.4 | −0.1 | 0.3 | −0.1 | −0.1 | 1.1 | −0.3 | −0.2 | 0.8 |
| Syrosingopine | 2469.136 nM | −0.1 | 0.0 | 0.5 | −0.1 | −0.1 | 1.1 | 0.0 | −0.1 | 2.2 |
| Syrosingopine | 823.045 nM | 0.0 | 0.0 | | 0.0 | 0.0 | | 0.0 | 0.0 | |
| Terconazole | 28000 nM | −0.9 | −1.2 | 1.3 | −1.1 | −0.9 | 0.8 | −0.8 | −1.0 | 1.2 |
| Terconazole | 9333.333 nM | −0.4 | −0.2 | 0.5 | −0.2 | −0.3 | 1.2 | −0.5 | −0.3 | 0.5 |
| Terconazole | 3111.111 nM | −0.1 | 0.0 | 0.2 | 0.0 | 0.0 | | −0.1 | 0.0 | 0.3 |
| Terconazole | 1037.037 nM | 0.0 | 0.0 | | 0.0 | 0.0 | | 0.0 | 0.0 | |
| Trimethylcolchicinic Acid | 44000 nM | −0.1 | −0.3 | 5.2 | −0.1 | −0.3 | 4.9 | −0.1 | −0.3 | 5.1 |
| Trimethylcolchicinic Acid | 14666.667 nM | 0.0 | −0.2 | 6.3 | 0.0 | −0.2 | 7.9 | 0.0 | −0.2 | 15.0 |
| Trimethylcolchicinic Acid | 4888.889 nM | 0.0 | 0.0 | | 0.0 | −0.1 | 3.7 | 0.0 | −0.1 | 12.0 |
| Trimethylcolchicinic Acid | 1629.63 nM | 0.0 | 0.0 | | 0.0 | 0.0 | | 0.0 | 0.0 | |

REFERENCES

Abizaid A, Albertal M, Costa M A, Abizaid A S, Staico R, Feres F, Mattos L A, Sousa A G, Moses J, Kipshidze N, Roubin G S, Mehran R, New G, Leon M B, Sousa J E. First human experience with the 17-beta-estradiol-eluting stent: the Estrogen And Stents To Eliminate Restenosis (EASTER) trial. J Am Coll Cardiol. 2004 Mar. 17; 43(6):1118-21.

Allen J N, Moore S A, Wewers M D. Taxol enhances but does not induce interleukin-1 beta and tumor necrosis factor-alpha production. J Lab Clin Med. 1993 October; 122(4):374-81.

Behrendt N. The urokinase receptor (uPAR) and the uPAR-associated protein (uPARAP/Endo180): membrane proteins engaged in matrix turnover during tissue remodeling. Biol. Chem. 2004 February; 385(2):103-36.

Belperio J A, Keane M P, Arenberg D A, Addison C L, Ehlert J E, Burdick M D, Strieter R M. CXC chemokines in angiogenesis. J Leukoc Biol. 2000 July; 68(1):1-8.

Castro V, Muriel P. Comparative study of colchicine and trimethylcolchicinic acid on prolonged bile duct obstruction in the rat. J Appl Toxicol. 1996 May-June; 16(3):269-75.

Chung E S, Packer M, Lo K H, Fasanmade A A, Willerson J T; Anti-TNF Therapy Against Congestive Heart Failure Investigators. Randomized, double-blind, placebo-controlled, pilot trial of infliximab, a chimeric monoclonal antibody to tumor necrosis factor-alpha, in patients with moderate-to-severe heart failure: results of the anti-TNF Therapy Against Congestive Heart Failure (ATTACH) trial. Circulation. 2003 Jul. 1; 107(25):3133-40.

Cipollone F, Ferri C, Desideri G, Paloscia L, Materazzo G, Mascellanti M, Fazia M, Iezzi A, Cuccurullo C, Pini B, Bucci M, Santucci A, Cuccurullo F, Mezzefti A. Preprocedural level of soluble CD40L is predictive of enhanced inflammatory response and restenosis after coronary angioplasty. Circulation. 2003 Dec. 2; 108(22):2776-82.

D'Amato R J, Lin C M, Flynn E, Folkman J, Hamel E. 2-Methoxyestradiol, an endogenous mammalian metabolite, inhibits tubulin polymerization by interacting at the colchicine site. Proc Natl Acad Sci USA. 1994 Apr. 26; 91(9):3964-8.

Deo R, Khera A, McGuire D K, Murphy S A, Meo Neto Jde P, Morrow D A, de Lemos J A. Association among plasma levels of monocyte chemoattractant protein-1, traditional cardiovascular risk factors, and subclinical atherosclerosis. J Am Coll Cardiol. 2004 Nov. 2; 44(9):1812-8.

Eubank T D, Galloway M, Montague C M, Waldman W J, Marsh C B. M-CSF induces vascular endothelial growth factor production and angiogenic activity from human monocytes. J. Immunol. 2003 Sep. 1; 171(5):2637-43.

Frantz, S. Playing dirty. Nature 2005, 437:942-943.

Garlichs C D, John S, Schmeisser A, Eskafi S, Stumpf C, Karl M, Goppelt-Struebe M, Schmieder R, Daniel W G. Upregulation of CD40 and CD40 ligand (CD154) in patients with moderate hypercholesterolemia. Circulation. 2001 Nov. 13; 104(20):2395-400.

Kunkel E J, Plavec I, Nguyen D, Melrose J, Rosler E S, Kao L T, Wang Y, Hytopoulos E, Bishop A C, Bateman R, Shokat K M, Butcher E C, Berg E L. Rapid structure-activity and selectivity analysis of kinase inhibitors by BioMAP analysis in complex human primary cell-based models. Assay Drug Dev Technol. 2004a, 2:431-41.

Kunkel E J, Dea M, Ebens A, Hytopoulos E, Melrose J, Nguyen D, Ota K S, Plavec I, Wang Y, Watson S R, Butcher E C, Berg E L. An integrative biology approach for analysis of drug action in models of human vascular inflammation. FASEB J. 2004b, 18:1279-81.

L'Allier P L, Tardif J C, Gregoire J, Joyal M, Lesperance J, Fortier A, Guertin M C. Sustained elevation of serum CD40 ligand levels one month after coronary angioplasty predicts angiographic restenosis. Can J Cardiol. 2005 May 1; 21(6):495-500.

Lennard, L. The clinical pharmacology of 6-mercaptopurine. Eur. J. Clin. Pharmacol., 43:329-339, 1992.

Ling, Y-H, Chan, J. Y., Beattie, K. L, and Nelson, J. A. Consequences of 6-thioguanine incorporation into DNA on polymerase ligase, and endonuclease reactions. Mol. Pharmacol., 42:802-807, 1992.

Morgan C J, Chawdry R N, Smith A R, Siravo-Sagraves G, Trewyn R W. 6-Thioguanine-induced growth arrest in 6-mercaptopurine-resistant human leukemia cells. Cancer Res. 1994 Oct. 15; 54(20):5387-93.

Pan S L, Huang Y W, Guh J H, Chang Y L, Peng C Y, Teng C M. Esculetin inhibits Ras-mediated cell proliferation and attenuates vascular restenosis following angioplasty in rats. Biochem Pharmacol. 2003 Jun. 1; 65(11):1897-905.

Rahimi N, Dayanir V, Lashkari K. Receptor chimeras indicate that the vascular endothelial growth factor receptor-1 (VEGFR-1) modulates mitogenic activity of VEGFR-2 in endothelial cells. J Biol. Chem. 2000 Jun. 2; 275(22):16986-92.

Serruys P W, Ormiston J A, Sianos G, Sousa J E, Grube E, den Heijer P, de Feyter P, Buszman P, Schomig A, Marco J, Polonski L, Thuesen L, Zeiher A M, Bett J H, Suttorp M J, Glogar H D, Pitney M, Wilkins G T, Whitbourn R, Veldhof S, Miquel K, Johnson R, Coleman L, Virmani R; ACTION investigators. Actinomycin-eluting stent for coronary revascularization: a randomized feasibility and safety study: the ACTION trial. J Am Coll Cardiol. 2004 Oct. 6; 44(7):1363-7.

Sousa J E, Serruys P W, Costa M A. New frontiers in cardiology: drug-eluting stents: Part I. Circulation. 2003a May 6; 107(17):2274-9.

Sousa J E, Serruys P W, Costa M A. New frontiers in cardiology: drug-eluting stents: Part II. Circulation. 2003b May 13; 107(18):2383-9.

Stefansson S, McMahon G A, Petitclerc E, Lawrence D A. Plasminogen activator inhibitor-1 in tumor growth, angiogenesis and vascular remodeling. Curr Pharm Des. 2003; 9(19):1545-64. Review.

Strauss B H, Lau H K, Bowman K A, Sparkes J, Chisholm R J, Garvey M B, Fenkell L L, Natarajan M K, Singh I, Teitel J M. Plasma urokinase antigen and plasminogen activator inhibitor-1 antigen levels predict angiographic coronary restenosis. Circulation. 1999 Oct. 12; 100(15):1616-22.

Wong S T, Baker L P, Trinh K, Hetman M, Suzuki L A, Storm D R, Bornfeldt K E. Adenylyl cyclase 3 mediates prostaglandin E(2)-induced growth inhibition in arterial smooth muscle cells. J Biol. Chem. 2001 Sep. 7; 276(36):34206-12.

Geisbuhler T P, Schwager T L, Rovetto M J. Guanosine metabolism in adult rat cardiac myocytes: inhibition by acyclovir and analysis of a metabolic pathway. J Mol Cell Cardiol. 1992 July; 24(7):683-90.

What is claimed is:

1. A method for identifying an agent useful in reducing the incidence of restenosis, said method comprising testing said agent in a plurality of in vitro assays that assess the ability of the agent to inhibit smooth muscle proliferation in an assay as recited in step (h) or (i); to not inhibit endothelial cell proliferation in an assay as recited in step (a), (b), (e), or (f); to inhibit matrix remodeling in an assay as recited in step (a), (c), (e), (g), (k), (l) or (m); to not act as a pro-thrombotic in an assay as recited in step (a), (e), (g), or (k); and to act as an anti-inflammatory in an assay as recited in step (a), (d), (e), (g), (i), (k), (l); wherein the assays are selected from:

(a) culturing umbilical vein endothelial cells in the presence of added IL-1β+TNF-α+IFN-γ, and recording changes in at least one cellular parameter readout as a result of introduction of the agent, said parameters being selected from: MCP-1, uPAR, tissue factor, thrombomodulin, SRB, and proliferation;

(b) culturing umbilical vein endothelial cells; and recording changes in proliferation as a result of introduction of the agent;

(c) culturing umbilical vein endothelial cells in the presence of added IL-4+histamine, and recording changes in at least one cellular parameter readout as a result of introduction of the agent, said parameters being selected from: VEGFRII, uPAR, and SRB;

(d) culturing peripheral blood mononuclear cells and umbilical vein endothelial cells in the presence of added TLR4, and recording changes in at least one cellular parameter readout as a result of introduction of the agent, said parameters being selected from: CD40, M-CSF, PGE2, TNF-α, and SRB;

(e) culturing coronary artery endothelial cells in the presence of added IL-1β+TNF-α+IFN-γ, and recording changes in at least one cellular parameter readout as a result of introduction of the agent, said parameters being selected from: MCP-1, CD 141, CD 142, IP-10, IL-8, tissue factor, thrombomodulin, SRB, and proliferation;

(f) culturing coronary artery endothelial cells and recording changes in proliferation as a result of introduction of the agent;

(g) culturing coronary artery smooth muscle cells cultured in the presence of added IL-1β+TNF-α+IFN-γ, and recording changes in at least one cellular parameter readout as a result of introduction of the agent, said parameters being selected from: MCP-1, uPAR, tissue factor, thrombomodulin, SRB and proliferation;

(h) culturing coronary artery smooth muscle cells and recording changes in proliferation as a result of introduction of the agent;

(i) culturing umbilical artery smooth muscle cells in the presence of added IL-1β+TNF-α+IFN-γ, and recording changes in at least one cellular parameter readout as a result of introduction of the agent, said parameters being selected from: MCP-1, CD141, CD142, IP-10, IL-8, SRB, and proliferation;

(j) culturing umbilical artery smooth muscle cells and recording changes in proliferation as a result of introduction of the agent;

(k) culturing umbilical vein endothelial cells and umbilical artery smooth muscle cells in the presence of added IL-1β+TNF-α+IFN-γ, and recording changes in at least one cellular parameter readout as a result of introduction of the agent, said parameters being selected from: CD40, uPAR, IP-10, tissue factor, thrombomodulin, M-CSF, and SRB;

(l) culturing fibroblasts cultured in the presence of added IL-1β+TNF-α+IFN-γ, and recording changes in at least one cellular parameter readout as a result of introduction of the agent, said parameters being selected from: Collagen I and IP-10;

(m) culturing fibroblasts in the presence of added TGF-β, and recording changes in at least one cellular parameter readout as a result of introduction of the agent, said parameters being selected from: Collagen I, SRB and PAI-1;

and wherein said agent is tested in at least one assay that assesses the ability of the agent to inhibit smooth muscle proliferation as recited in steps (g), (h), (i) and (j) and at least one assay that assesses the ability of the agent to not inhibit endothelial cell proliferation as recited in steps (a), (b), (c) (d), (e), and (f), wherein an agent that inhibits smooth muscle proliferation and does not inhibit endothelial cell proliferation is selected as being useful in reducing the incidence of restenosis.

2. The method of claim 1, wherein the cellular parameter readout is selected from uPAR expression of endothelial cells or smooth muscle cells; PGE$_2$ expression in endothelial cells or monocytes; thrombomodulin expression in endothelial cells and smooth muscle cells, tissue factor expression in endothelial cells and smooth muscle cells, CD40 expression in monocytes or endothelial cells; IP-10 expression in endothelial cells or human dermal fibroblasts; MCP-1 expression in vascular endothelial cells or smooth muscle cells, collagen I expression in human dermal fibroblasts; VEGFR2 expression in endothelial cells; PAI-1 expression in human dermal fibroblasts or smooth muscle cells; IL-8 expression in smooth muscle cells; M-CSF expression in endothelial cells or smooth muscle cells, TNF-α expression in monocytes.

3. The method of claim 1, wherein each assay is scored according to modulation of the selected readout parameters, and wherein an agent that scores higher than a control compound that is an approved therapeutic agent for inhibition of restenosis.

4. The method of claim 1, further comprising determining a log ratio of smooth muscle cell to endothelial cell proliferation for the compounds, where an agent having a ratio of greater than 1 preferentially inhibit smooth muscle cell proliferation relative to endothelial cell proliferation and is selected as a candidate drug.

5. A method for identifying an agent useful in reducing the incidence of restenosis, said method comprising testing said agent in a plurality of in vitro assays that assess the ability of the agent to inhibit smooth muscle proliferation in an assay as recited in step (d) or (e); to not inhibit endothelial cell proliferation in an assay as recited in step (a), (b); to inhibit matrix remodeling in an assay as recited in step (a) or (d); to not act as a pro-thrombotic in an assay as recited in step (a) or (d); and to act as an anti-inflammatory in an assay as recited in step (a), (c), or (d); wherein the assays comprise each of:

(a) culturing umbilical vein endothelial cells in the presence of added IL-1β+TNF-α+IFN-γ, and recording changes in at least one cellular parameter readout as a result of introduction of the agent, said parameters being selected from: MCP-1, uPAR, tissue factor, thrombomodulin, SRB, and proliferation;

(b) culturing umbilical vein endothelial cells; and recording changes in proliferation as a result of introduction of the agent;

(c) culturing peripheral blood mononuclear cells and umbilical vein endothelial cells cultured in the presence of added TLR4, and recording changes in at least one cellular parameter readout as a result of introduction of the agent, said parameters being CD40, M-CSF, PGE2, TNF-α, and SRB;

(d) culturing coronary artery smooth muscle cells cultured in the presence of added IL-1β+TNF-α+IFN-γ, and recording changes in at least one cellular parameter readout as a result of introduction of the agent, said parameters being: MCP-1, uPAR, tissue factor, thrombomodulin, SRB and proliferation;

(e) culturing coronary artery smooth muscle cells and recording changes in proliferation as a result of introduction of the agent;

and wherein an agent that inhibits smooth muscle proliferation in one of the foregoing assays and does not inhibit endothelial cell proliferation in one of the foregoing assays is selected as being useful in reducing the incidence of restenosis.

* * * * *

UNITED STATES PATENT AND TRADEMARK OFFICE
CERTIFICATE OF CORRECTION

PATENT NO.        : 8,697,387 B2                              Page 1 of 1
APPLICATION NO.   : 12/302756
DATED             : April 15, 2014
INVENTOR(S)       : Eric J. Kunkel et al.

It is certified that error appears in the above-identified patent and that said Letters Patent is hereby corrected as shown below:

IN THE CLAIMS:

Column 29, line 62 (Claim 1, line 69) "IL-1β+TNF-α+IFN-γ," should read
--IL-1β+TNF-α+IFN-γ+TGF-β,--.

Signed and Sealed this
Twenty-third Day of September, 2014

Michelle K. Lee
*Deputy Director of the United States Patent and Trademark Office*